United States Patent [19]

Rosenthal

[11] 4,379,233
[45] Apr. 5, 1983

[54] OPTICAL ARRANGEMENT FOR QUANTITATIVE ANALYSIS INSTRUMENT UTILIZING PULSED RADIATION EMITTING DIODES

[75] Inventor: Scott B. Rosenthal, Gaithersburg, Md.

[73] Assignee: Trebor Industries, Inc., Gaithersburg, Md.

[21] Appl. No.: 267,555

[22] Filed: May 27, 1981

[51] Int. Cl.³ .............................................. H01L 9/00
[52] U.S. Cl. ................................. 250/553; 250/223 R
[58] Field of Search .............. 250/553, 552, 573, 574, 250/575, 223 R; 313/500; 362/800, 240

[56] References Cited
U.S. PATENT DOCUMENTS
4,229,103 10/1980 Hipp ..................................... 250/553

Primary Examiner—David C. Nelms
Assistant Examiner—Darwin R. Hostetter
Attorney, Agent, or Firm—Bernard, Rothwell & Brown

[57] ABSTRACT

An instrument for quantitative analysis using a matrix of radiation emitting diodes has means for assuring that a sample receives substantially uniform radiation from each diode. In the preferred embodiment a lens is used to direct the radiation beams to a focal plane where there is a matte surface diffuser backed with an aperture to provide relatively uniform radiant energy field through the aperture to a sample chamber. With this arrangement the same energy distribution contacts the test samples from each of the radiation sources.

6 Claims, 8 Drawing Figures

OPTICAL ARRANGEMENT FOR QUANTITATIVE ANALYSIS INSTRUMENT UTILIZING PULSED RADIATION EMITTING DIODES

BACKGROUND OF THE INVENTION

1. Field of the Invention

This invention relates to improvements in quantitative analysis instruments utilizing a plurality of radiation emitting diodes such as IREDs and particularly to an optical arrangement for such instruments to assure that the energy distribution on the test samples is the same from each of the IREDs.

2. Description of the Prior Art

There are known in the prior art instruments for quantitative analysis utilizing near infrared radiation energy. These instruments can measure chemical constituents in a sample by either reflecting the radiant energy off the product or transmitting it through the product. Such instruments utilize a phenomenon that certain organic substances absorb energy in particular portions of the spectrum. By measuring the amount of energy absorbed by the sample at certain specific wavelengths, precise quantitative measurements of the constituents in the sample can be determined. For example, the measurement of protein content in wheat can be performed in this manner. For a general introduction to near infrared quantitative analysis, see the paper presented by Robert D. Rosenthal to the 1977 Annual Meeting of American Association of Cereal Chemists entitled "An Introduction to Near Infrared Quantitative Analysis".

In prior application, Ser. No. 73,965 filed Sept. 10, 1979 there is disclosed an apparatus for near infrared quantitative analysis utilizing pulsed infrared emitting diodes (IREDs). Reference may be had to this application for further prior art and background information.

When utilizing multiple IREDs in a near infrared quantitative analysis instrument it is desirable to mount them in a geometric array or a matrix. However, because each IRED does not emit parallel light the radiation falling on the sample may vary from IRED to IRED thus creating a variation in the readings from the instrument. Attempts to correct these problems can involve expensive optical elements. Thus, there is need in the art for the use of low-cost simple elements that can provide identical accuracy, precision and energy distribution on the sample. This need arises from the technical problem in that the individual light elements (for example the IREDs) typically have collimating lenses built into them. The purpose of such lenses is to provide a light beam that is as parallel as possible. However, due to practical limitations in optics including atmospheric dissipation the light emitted is never truly parallel and typically emanates at angles up to 8 degrees off of a parallel path. The light exiting from these lenses tends to have large scattering patterns near the focal point and this causes uneven energy distribution on the test samples.

SUMMARY OF THE INVENTION

This invention utilizes a matrix of individual pulsed radiation emitting diodes for directing radiation toward a sample in a sample chamber in an instrument for quantitative analysis which would have photodetection means, readout, etc. The optical arrangement which is the feature of this invention includes a means for directing the radiation from each of the diodes upon the sample with equal intensity. This may be accomplished with a large lens system, or preferably with a Fresnel lens directing radiation toward a focal plane in front of the sample. A matte surface diffuser is positioned at the focal plane and is backed up with an aperture in front of the sample chamber. This arrangement provides relatively uniform radiant energy through the aperture and an even energy distribution on the sample in the sample chamber. In the preferred embodiment there are two such diffusers separated at a small distance backed by the aperture.

DESCRIPTION OF THE PREFERRED EMBODIMENT

Figure 1:
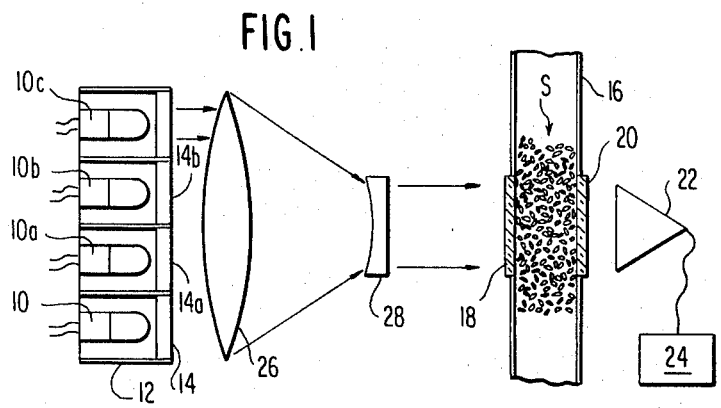
FIG. 1 is a schematic side elevational view illustrating some of the principles of this invention.
Figure 2:
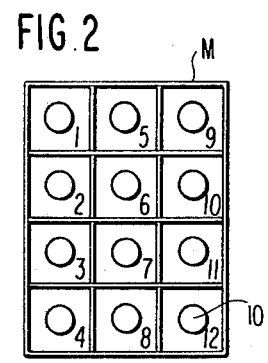
FIG. 2 is a front elevational view showing a matrix of the radiant energy emitters.

The invention is useful in a near infrared quantitative analysis instrument of the type disclosed in the Rosenthal et al application, Ser. No. 73,965, filed Sept. 10, 1979. Such instrument utilizes a plurality of pulsed infrared emitting diodes (IREDs) with narrow bandpass filters to direct radiant energy through a grain sample toward a detector. The energy is detected, and depending on the absorption at particular wavelengths, the chemical constituents can be measured and the measurements displayed. It is in the environment of such instrument, which is now commercially available on the market as the Trebor 90 from Trebor Industries, Inc. in Gaithersburg, Md., that the present invention applies. As shown in FIG. 1 there is an instrument with a plurality of IREDs 10a, 10b, 10c, etc. which as shown in FIG. 2 are positioned in a four by three matrix. These individual IREDs are separated light-wise from each other by baffles 12 and their radiation is directed to the right as viewed in FIG. 1 through individual narrow bandpass filters 14.

A sample chamber 16 containing a sample S, for example grain, has windows 18 and 20 which are transparent to the radiation. A stop gate, not shown, holds the sample in the chamber during measurement.

On the side of the sample chamber opposite the IREDs there is a photodetector means 22 to detect the radiation passing through the sample in the sample chamber. The photodetection means is connected to a means 24 for calculating and displaying the result of the quantitative analysis. The foregoing is more fully disclosed in the application of Rosenthal et al. Ser. No. 73,965, filed Sept. 10, 1979.

Figure 3A:
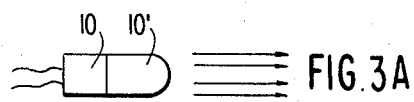
FIGS. 3A and 3B are schematic views of the ideal and actual radiation emitters, respectively.
Figure 3B:

FIGS. 3A and 3B show the ideal IRED and the practical IRED. Typically IREDs have collimating lenses 10' built into them. The purposes of such lenses is to provide a light beam that is as parallel as possible. However, because of practical limitations in optics the light emitted is not truly parallel and typically emanates from the IREDs at angles of up to 8 degrees off of a parallel path as shown schematically in FIG. 3B.

Figure 4:
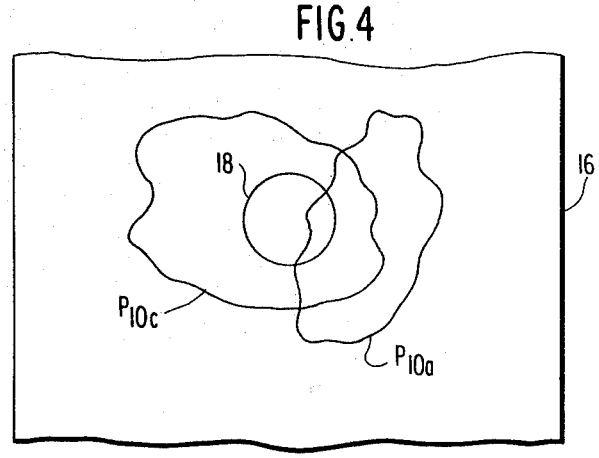
FIG. 4 is an elevational view of the light distribution from IREDs without the use of this invention.

FIG. 4 illustrates the practical problem which occurs when the light beams from the IREDs are not truly parallel. This shows the sample chamber 16 and window 18 with schematic illustrations, for example of a light pattern from IRED 10a, P10a and a light pattern from IRED 10c, P10c. It is seen that the light emitting from the lens 10' of the IRED 10 tends to have a large scattering pattern near the focal plane. That is, the pattern of light from the individual IREDs because of the nonparallel nature of such light tends to be scattered over an area considerably larger than is needed from a measurement standpoint.

One solution to the problem which is within the scope of the invention but not the preferred embodiment is shown in FIG. 1. In that case there is a large convex converging lens 26 which converges the light from the matrix M of IREDs and a smaller lens 28 to provide parallel light exiting from that lens which passes toward the window 18.

Figure 5:
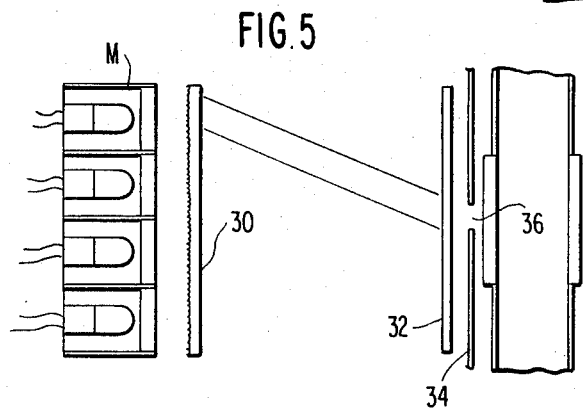
FIG. 5 is a side elevational view of the present invention in its simplest form.
Figure 6:
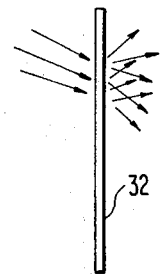
FIG. 6 is a schematic view showing the effect of utilizing a diffusing material in the focal plane.

The preferred embodiment of the overall invention is illustrated in FIG. 5. In this embodiment there is the same matrix M of IREDs, baffles and narrow bandpass filters as in FIGS. 1 and 2. In place of the dual lens system of FIG. 1, however, the preferred embodiment utilizes a Fresnel lens 30 to direct the light from the IREDs on a focal plane diffuser 32. That is, the Fresnel lens directs the radiation from each of the IREDs and focuses it at a focal plane. In the focal plane there is positioned a diffusing plate 32. The plate 32 is of a diffusing material, for example a matte surface, and the result is that such diffusing material causes light to be emitted in all directions essentially with uniform energy. This is schematically illustrated in FIG. 6.

In FIG. 5 between the diffusing plate 32 and the sample chamber 16 there is an opaque material or sheet 34 with a single small aperture 36 positioned in front of, but smaller than the window 18. The material of diffusing plate 32 can be, for example, a translucent plexiglass where the surface has been rough-sanded to provide a diffuser, i.e., a matte finish. The pattern of light because of the nonparallel nature of the IRED light tends to be scattered over an area considerably larger than is needed from a measurement standpoint. To minimize this problem the opaque plate 34 having aperture 36 in it, is placed on the side of the diffusing plate adjacent the sample. This aperture 36 limits the amount of light that the sample can "see" and thus, tends to only let the light from the same direction contact the sample.

Figure 7:
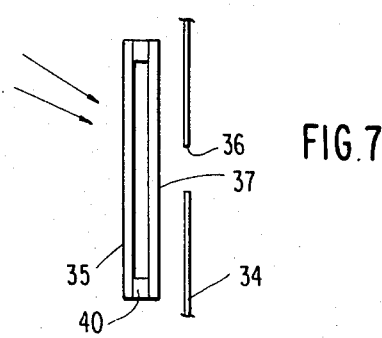
FIG. 7 is a sectional elevation of a preferred embodiment of the diffuser to be used in the focal plane.

A preferred embodiment of the diffuser means is a pair of diffuser plates as shown in FIG. 7. In this figure there is a diffuser plate 35 closest to the IREDs and a spaced-apart diffuser plate 37 closest to the apertured plate 34. A spacer 40, for example 1/16th inch thick, spaces the two diffusers. In this embodiment the scattered light from the diffuser 35 is spread more evenly by the diffuser 37, and thus, the light emitting from the second diffuser through the aperture 36 is essentially uniform in nature and can be used for exacting measurement requirements in the field of near infrared quantitative analysis.

A nonlimiting example of the invention in the preferred embodiment has been implemented in a commercially available Trebor 90 Grain Tester implement first sold in December 1980, with the following details. 12 GE 1N6264 IREDs are mounted in a three by four array, one-half inch on center. In front of each IRED is a narrow bandpass filter that only allows a specific wavelength of light to pass. A Fresnel lens from Edmund Scientific No. 30389 is placed in the light beam so that the light from all 12 sequentially illuminated IREDs passes through the Fresnel lens. The Fresnel lens bends the light so that the light from each of the 12 IREDs comes close to a theoretical focal point of the lens. At this focal point two diffuser plates (each one a sanded piece of plexiglass from Rohm & Haas No. 7204) are separated by 1/16th inch spacer. A 5/8th inch aperture is provided so that only light through that aperture can exit from the optical arrangement. A test sample in a sample chamber can be placed essentially at any distance including extremely small distances from the aperture. In the Trebor 90 the distance of a test sample is approximately 1/16th inch away from the aperture plate.

Although the above invention has been described in connection with pulsed infrared light emitting diodes, the invention has also applicability for other radiation-emitting diodes used in such instruments, such as light-emitting diodes (LEDs).

I claim:

1. An instrument for quantitative analysis of a sample comprising:
    a plurality of pulsed radiation emitting diodes positioned in a matrix to direct radiation to a sample;
    baffles separating the diodes in the matrix;
    narrow bandpass filters positioned adjacent the diodes to allow only preselected wavelengths of radiation to be directed to the sample;
    a sample chamber having at least portions thereof transparent to the radiation from the diodes and bandpass filters;
    lens means positioned adjacent the matrix of diodes and bandpass filters to that radiation from all of the diodes passes through the lens and is bent toward the center of a focal plane adjacent the sample chamber;
    radiation altering means to allow radiation from the lens means to pass to the sample but with uniform energy distribution from each of the diodes;
    photodetecting means for detecting the radiation which passes through a sample in the sample chamber;
    means to calculate and display quantitative analysis based on the output of the photodetecting means.

2. An instrument as in claim 1 wherein the radiation altering means is a light diffusing plate means positioned substantially at the focal point of the lens means.

3. An instrument as in claim 2 further comprising an opaque plate with a small aperature positioned between the light diffusing plate means and the sample chamber.

4. An instrument as claimed in claim 2 wherein the light diffusing plate means is a pair spaced apart diffuser plates.

5. An instrument as claimed in claim 4 wherein each diffuser plate is transparent plastic with a nonglossy matte surface on each side thereof.

6. An instrument as claimed in claim 1 wherein the lens means is a Fresnel lens.

* * * * *